United States Patent
Kinebuchi et al.

(10) Patent No.: US 9,801,963 B2
(45) Date of Patent: Oct. 31, 2017

(54) STEAM STERILIZER

(75) Inventors: Chihiro Kinebuchi, Chikuma (JP);
Eiichi Minemura, Chikuma (JP);
Satoshi Tanaka, Chikuma (JP); Haruo Machida, Chikuma (JP); Akihiro Miyamoto, Chikuma (JP); Kouji Tanaka, Chikuma (JP); Hiroshi Karasawa, Chikuma (JP)

(73) Assignee: SAKURA SEIKI CO., LTD., Nagano (JP)

( * ) Notice: Subject to any disclaimer, the term of this patent is extended or adjusted under 35 U.S.C. 154(b) by 343 days.

(21) Appl. No.: 14/371,555

(22) PCT Filed: Jan. 30, 2012

(86) PCT No.: PCT/JP2012/052016
§ 371 (c)(1),
(2), (4) Date: Jul. 10, 2014

(87) PCT Pub. No.: WO2013/114539
PCT Pub. Date: Aug. 8, 2013

(65) Prior Publication Data
US 2014/0363339 A1 Dec. 11, 2014

(51) Int. Cl.
*A61L 2/07* (2006.01)
*F04F 5/04* (2006.01)
*F04F 5/20* (2006.01)

(52) U.S. Cl.
CPC ... *A61L 2/07* (2013.01); *F04F 5/04* (2013.01); *F04F 5/20* (2013.01)

(58) Field of Classification Search
CPC ............ A61L 2/07; F04F 5/04; F04F 5/20
See application file for complete search history.

(56) References Cited

U.S. PATENT DOCUMENTS

| | | | | |
|---|---|---|---|---|
| 4,687,635 A | * | 8/1987 | Kaehler | A61L 2/24 422/110 |
| 4,999,165 A | * | 3/1991 | Calabra | B01J 3/03 422/113 |
| 2009/0288721 A1 | * | 11/2009 | Brugnoli | A61L 2/07 137/563 |

FOREIGN PATENT DOCUMENTS

JP  63311959  12/1988
JP  2794361   9/1998
(Continued)

OTHER PUBLICATIONS

Sakura Seiki Co., Ltd., International Search Report mailed Apr. 24, 2012 for PCT/JP2012/052016.

*Primary Examiner* — Timothy Cleveland
(74) *Attorney, Agent, or Firm* — Blakely Sokoloff Taylor & Zafman; Tom Babbitt

(57) ABSTRACT

Provided is a steam sterilizer capable of performing water vapor sterilization without using a vacuum pump as a mechanism for bringing the inside of a pressure vessel into vacuum. The steam sterilizer includes a pressure vessel (32) which stores an object to be sterilized and in which sterilization is performed with water vapor supplied from a steam piping, and vacuum-generating means (34) which is connected to the pressure vessel (32) and brings the inside of the pressure vessel (32) into a vacuum state. The vacuum-generating means (34) includes a water ejector (48), a tank (50) for storing supply water supplied from an outside, and a pump (52) for supplying the supply water inside the tank (50) to the water ejector (48).

10 Claims, 3 Drawing Sheets

(56) References Cited

FOREIGN PATENT DOCUMENTS

| JP | 2000199490 | 7/2000 |
|----|------------|--------|
| JP | 2004016035 | 1/2004 |

* cited by examiner

STEAM STERILIZER

CROSS-REFERENCE TO RELATED APPLICATION

This application is a non-provisional application claiming the benefit of International Patent Application No. PCT/JP2012/052016, filed Jan. 30, 2012.

TECHNICAL FIELD

The present invention relates to a steam sterilizer for sterilizing an object to be sterilized with water vapor.

BACKGROUND ART

In hospitals and so on, sterilization processing needs to be performed on objects to be sterilized such as a bandage for treatment, a scalpel, a pair of forceps, and a surgical gown that need to be sterilized. The steam sterilizers including a pressure vessel that stores the objects to be sterilized are often used to sterilize such objects to be sterilized as described above.

General steam sterilizers act to sterilize the object to be sterilized by introducing saturated water vapor into the pressure vessel to pressurize and heat it, and keeping a predetermined pressure and temperature for a certain time (refer to, e.g., patent literature 1).

The steam sterilizer described in Patent Literature 1 is the pressure vessel having a double-can structure including an inner can and an outer can forming a sterilization chamber that stores the object to be sterilized. A jacket portion is provided between the inner can and the outer can of the pressure vessel, and the saturated water vapor is introduced into the jacket portion. The inner can is heated with the saturated water vapor introduced into the jacket portion.

Further, the saturated water vapor is introduced also into an inner portion of the inner can. The inner can is pressurized and heated up to the predetermined pressure with the introduced saturated water vapor, and heated up to the predetermined temperature by the jacket portion around the inner can.

The inner can is kept at the predetermined pressure and the predetermined temperature with the saturated water vapor for the certain time, so that the sterilization is performed on the object to be sterilized stored in the inner can. After the certain time has elapsed, a gas-discharging process for discharging the saturated water vapor from the inner can is performed. In the inner can set in a vacuum state by the gas-discharging process, moisture adhering to the object to be sterilized is evaporated to dry it.

As described in Patent Literature 1, in the gas-discharging process, the saturated water vapor in the inner can is generally discharged by a vacuum pump.

Gas in the inner can is discharged by the vacuum pump not only when the gas-discharging process is performed, but also when a pre-warming process (conditioning process) is performed prior to performing the sterilization. In the pre-warming process, first, the inner can is brought into the vacuum state by the vacuum pump, the saturated water vapor is introduced from the jacket portion, and then a pressure of the inner portion of the inner can is raised to an atmosphere pressure with the saturated water vapor. The vacuum pump is driven to bring the inner can into the vacuum state again. This action is repeatedly performed a plurality of times to sufficiently pre-warm the object to be sterilized, and further replace air remaining inside the inner can with the water vapor, so that atmosphere in the inner can becomes closer to the saturated water vapor state.

PRIOR TECHNICAL LITERATURE

Citation List Patent Literature

Patent Literature 1: Japanese Patent Laid-Open No. 2000-199490

SUMMARY OF INVENTION

Technical Problem

In such a conventional steam sterilizer as being disclosed in Patent Literature 1, the gas in an inside of the pressure vessel is discharged using the vacuum pump, which causes a problem that another power source (AC200V) for driving the pump is required, thereby making an equipment larger, and thus a desire for reducing a power consumption cannot be realized.

Therefore, the present invention is made to solve the above-described problem, and the object thereof is to provide a steam sterilizer as a mechanism for bringing the inside of a pressure vessel into a vacuum state without using the vacuum pump.

Solution to Problem

A steam sterilizer according to the present invention includes a pressure vessel which stores an object to be sterilized and in which sterilization is performed with water vapor supplied from a steam piping; and vacuum-generating means which is connected to the pressure vessel and brings an inside of the pressure vessel into a vacuum state, wherein the vacuum-generating means includes a water ejector, a tank for storing supply water supplied from an outside, and a pump for supplying the supply water in the tank to said water ejector.

By adopting the above-described configuration, and by using a water ejector to bring the inside of the pressure vessel into a vacuum state, another power source for the vacuum-generating means is not required, thereby reducing the equipment in size and making contribution to cutting the power consumption.

Further, it may be characterized in that the tank has a temperature sensor provided for detecting a temperature inside the tank, a gas and water discharging system connected thereto from said pressure vessel to introduce the discharged gas and water from the pressure vessel, and a control valve provided for controlling introduction of the supply water from said outside, in a case where it is detected that the temperature detected by said temperature sensor due to the introduction of the discharged gas and water from the pressure vessel is higher than a threshold value previously set due to the introduction of the discharged gas and water from the pressure vessel.

In the conventional steam sterilizer, since the discharged gas and water discharged from the inside of the pressure vessel by the vacuum pump has a high temperature, a dedicated water-discharging equipment is required, thereby increasing an initial cost. Further, particularly, when the discharged gas and water are cooled, a great amount of water is required for an equipment of a water-cooling type, thereby increasing running costs. However, by adopting such a configuration, the tank of the water to be supplied to the water ejector and the tank for discharging the water from the pressure vessel can be used in common, and thus the discharged water can be cooled without necessity of the dedicated water-discharging equipment, thereby reducing the initial cost. Furthermore, since cooling the discharged gas and water from the pressure vessel and controlling the temperature of the water to be supplied to the water ejector can be simultaneously performed in one tank, an amount of water usage can be reduced, thereby reducing the running costs. As described above, according to the above-described configuration, processing of discharging air and water at the high temperature can be performed at low costs.

Furthermore, it may be characterized in that a pipe for supplying the supply water from the outside to the tank is connected to a piping of the discharged gas and water system from the pressure vessel.

In other words, when the steam from the inner can, of the discharged gas and water from the pressure vessel, is discharged into the tank storing the water, a water-hammering operation occurs to rapidly condense the steam in the tank, thereby generating noise and vibrations. However, the water-hammering operation can be prevented by condensing discharged gas and steam in the piping, since water-supply action is forcibly performed in a gas-discharging action by adopting the above-described configuration in which a water-supplying circuit is connected to a discharge side of the water ejector used for discharging the gas from the inner can.

Moreover, it may be characterized in that condensing means for condensing the water vapor in the discharged gas from the pressure vessel is provided at a side of the pressure vessel of the water ejector.

Discharging the gas by the water ejector generally takes longer than discharging the gas by the vacuum pump. However, by providing the condensing means at a primary side of the water ejector to condense the water vapor in the discharged gas, a discharging speed and a vacuum-reaching level can be improved.

Further, it may be characterized in that a door for opening/closing an opening portion is provided for said pressure vessel, a packing in contact with an inner face of said door when the door is closed is provided at a periphery of the opening portion of said pressure vessel, and a steam piping is branched and arranged inside the packing so that, when said door is closed, the packing is pressed and moved to the inner face of the door by the water vapor from said steam piping.

In the conventional steam sterilizer, the packing is generally driven with pressured air. However, even if a small amount of the pressured air for driving leaks via the packing into the pressure vessel, the sterilization may be failed. However, according to the above-described configuration, even if a small amount of water vapor should leak via the packing into the pressure vessel, the sterilization cannot be failed since the same water vapor is used as that of the sterilization agent.

Advantageous Effects of Invention

According to the steam sterilizer of the present invention, since the water ejector is used without using the vacuum pump as the mechanism for bringing the inside of the pressure vessel into the vacuum state, providing the another power source for the vacuum-generating means is not required and the equipment can be reduced in size, thereby making the contribution to reducing the power consumption.

DESCRIPTION OF EMBODIMENTS

With reference to diagrams, the steam sterilizer according to the present embodiment will be described below.

Figure 1:
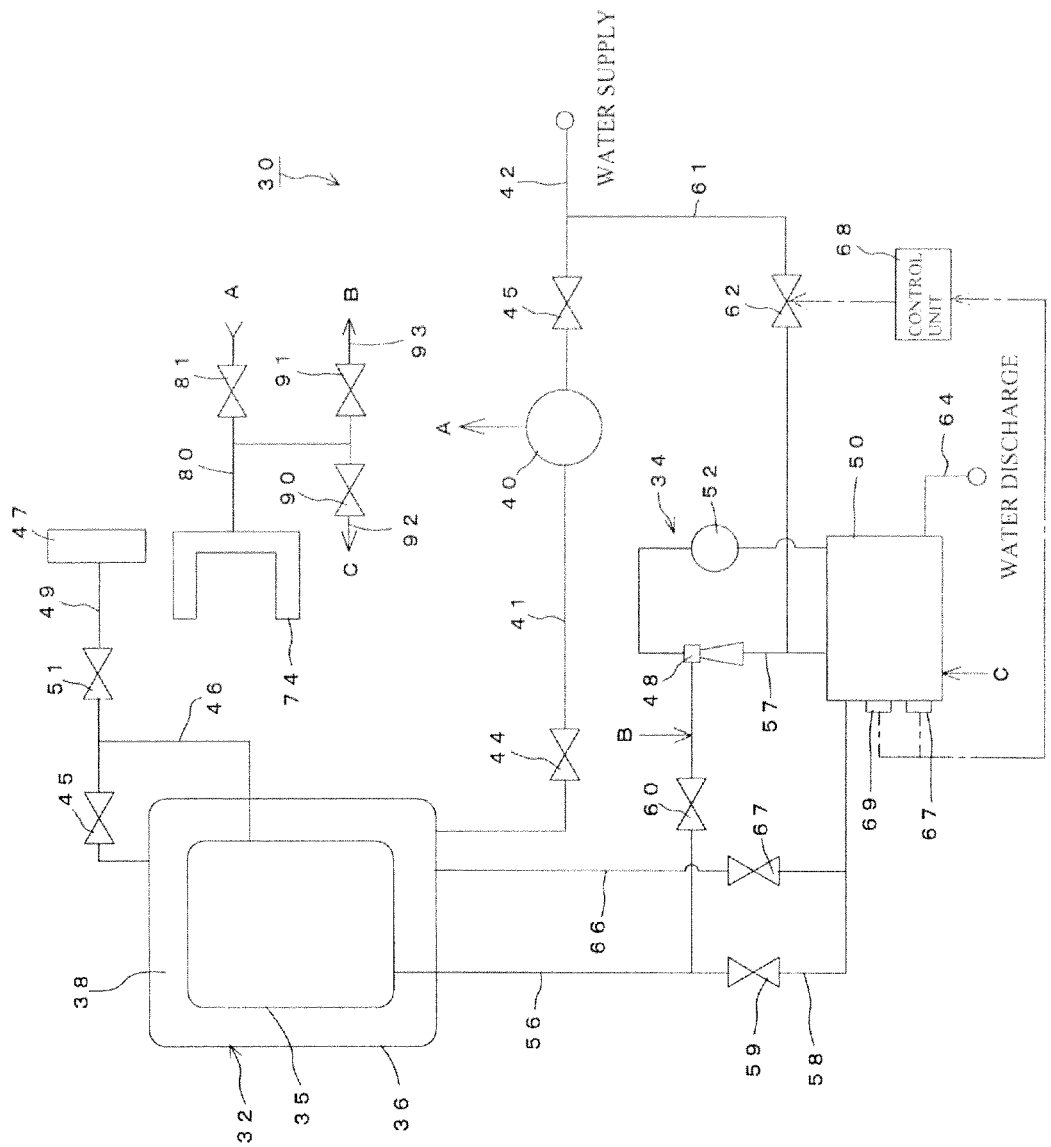
FIG. 1 is a schematic line diagram of a first embodiment of a steam sterilizer.

FIG. 1 is a schematic line diagram illustrating a configuration of the steam sterilizer.

A steam sterilizer 30 includes a pressure vessel 32 storing an object to be sterilized, and vacuum-generating means 34 which is connected to the pressure vessel 32 and brings an inside of the pressure vessel 32 into a vacuum state.

The pressure vessel 32 has a double-can structure including an inner can 35 and an outer can 36, and a gap therebetween is a jacket portion 38. Inside the inner can 35, an object to be sterilized, such as a bandage, a scalpel, a pair of forceps, and a surgical gown, is stored. In the jacket portion 38, the saturated water vapor described below is introduced and the inner can 35 is heated up to a predetermined temperature, and then the temperature can be kept.

Steam piping 41 for introducing the saturated water vapor generated by a steam-generating device 40 is connected to the jacket portion 38. The steam piping 41 is provided with a steam-supply valve 44 for controlling the introduction of the saturated water vapor to the jacket portion 38 by opening/closing the steam piping 41.

According to the present embodiment, the steam-generating device 40 includes an electric heater for heating water, and water piping 42 for supplying the water from the outside is connected to the steam-generating device 40. Further, the water piping 42 is provided with a water-supply valve 45 capable of opening/closing the water piping 42 to control supply of the water to the steam-generating device 40.

As to the supply of the water to the steam-generating device 40, processed water such as soft water or Reverse Osmosis (RO) water may be supplied to the steam-generating device 40 to reduce scale adhering onto an inside of the steam-generating device 40. In such a case, the water piping 42 via which the water is supplied from the outside may be divided into two systems, and may be connected to the piping to supply the processed water to the primary side of the water-supply valve 45 (not illustrated).

The pressure vessel 32 is provided with steam piping 46 for connecting the jacket portion 38 with the inner can 35 to supply the saturated water vapor in the jacket portion 38 into the inner can 35. At a middle portion of the steam piping 46, the steam-supply valve 45 for controlling the supply of the saturated water vapor to the inner can 35 is provided.

Further, an air-supply pipe 49 capable of supplying air via an air filter 47 is connected to the steam piping 46. At a middle portion of the air-supply pipe 49, an air-supply pipe 51 for controlling the supply of the air is provided.

The vacuum-generating means 34 according to the present embodiment includes a water ejector 48, a tank 50 for storing the supply water supplied from the outside, and a pump 52 for supplying the supply water in the tank 50 to the water ejector 48.

Figure 2:
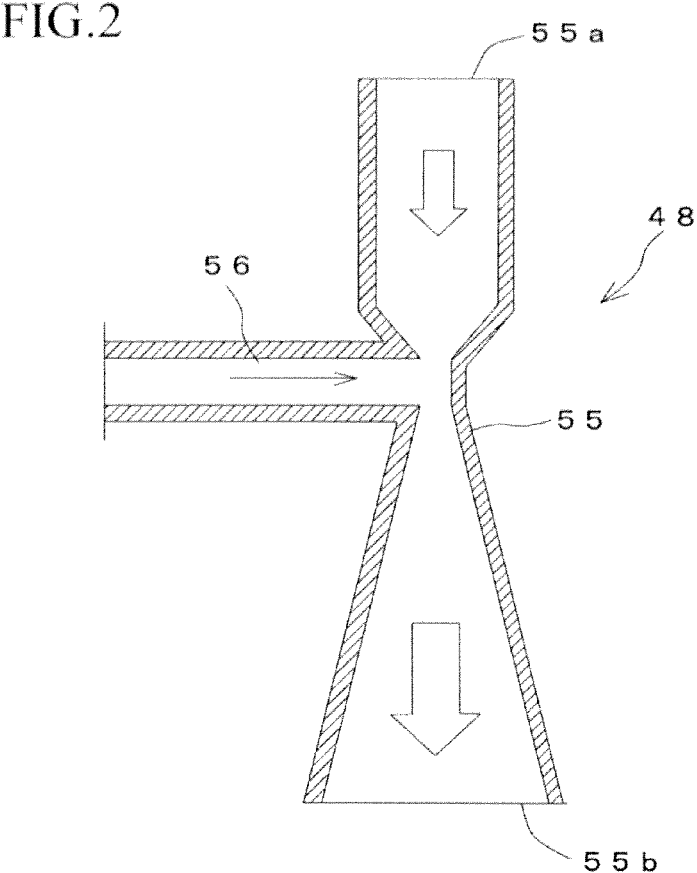
FIG. 2 is an explanation diagram illustrating a configuration of a water ejector.

The water ejector 48 can adopt a configuration that is generally known. The water ejector 48 according to the present embodiment, as illustrated in FIG. 2, includes a nozzle 55 formed in a T-like shape, and the water pressurized by the pump 52 is introduced into a nozzle inlet 55a illustrated in a top portion of the diagram.

A diameter of a flow path of the nozzle 55 becomes thinner at a middle portion between the inlet 55a and an outlet 55b. A gas and water discharging pipe 56 (gas and water discharging pipe inside the inner can 35) from the pressure vessel 32 is connected to a thinner portion.

When the water pressurized by the pump 52 is supplied into the inlet 55a of the nozzle 55, at a portion where the nozzle 55 becomes thinner, a flowing speed becomes faster according to a principle of Venturi, and thus the discharged gas from the pressure vessel 32 is absorbed via the gas and water discharging pipe 56.

At the outlet 55b of the nozzle 55, a water-discharging pipe 57 connected to the tank 50 is provided. In the water-discharging pipe 57, the water from the tank 50 that has passed through the nozzle 55 and the air and the water discharged from the gas and water discharging pipe 56 flow. Therefore, in the tank 50, the water that is an actuation fluid of the water ejector 48 can return via the water-discharging pipe 57, and further the discharged gas and water from the pressure vessel 32 can be stored also in the tank 50.

The gas and water discharging pipe 56 from the inner can 35 of the pressure vessel 32 is provided with a branch pipe 58 that is branched from the pipe connected to the water ejector 48 described above and is directly connected to the tank 50.

At a side of the branch pipe 58 and a side connected to the water ejector 48 of the gas and water discharging pipe 56, valves 59, 60 capable of opening/closing each pipe are provided respectively. By an opening/closing action of the valves 59, 60, the inside of the inner can 35 is brought into the vacuum state. In addition, the water can be directly discharged from the inner can 35 to the tank 50.

A branch pipe 61 branched from the water piping 42 is connected to the tank 50 and the water from the outside is supplied and stored in the tank 50. At a middle portion of the branch pipe 61, a valve 62 for opening/closing the branch pipe is provided. Further, the tank 50 is provided with a water-discharging pipe 64 and the water in the tank 50 can be discharged.

According to the present embodiment, the branch pipe 61 of the water piping 42 for supplying the water from the outside to the tank 50 is connected to the water-discharging pipe 57 at the discharge side of the water ejector 48. As described above, the branch pipe 61 for supplying the water to the tank 50 is connected to the water-discharging pipe 57 of the water ejector 48 to prevent the water-hammering operation. More details will be described on this point. If the steam from the inner can 35 is discharged into the tank 50 as it is, the steam is rapidly cooled and condensed in the tank 50 and, then, the pressure is reduced. Thus, if the water is rapidly supplied when the pressure is reduced, shock and noise will be caused. However, since the branch pipe 61 for supplying the water is connected to the water-discharging pipe 57 of the water ejector 48, by an operation of the water ejector 48, the water from the branch pipe 61 is forcibly supplied to the water-discharging pipe 57. Therefore, according to this configuration, the steam discharged in the water-discharging pipe 57 can be condensed to prevent the water-hammering operation.

Further, a drain-discharging pipe 66 for discharging drain in the jacket portion 38 is connected to the tank 50.

The drain-discharging pipe 66 is provided with a steam trap 67, and only the drain is discharged from atmosphere including the steam and the steam is not discharged via the drain-discharging pipe 66 as much as possible.

As described above, the gas and water discharging pipe 56 from the inner can 35 and the drain-discharging pipe 66 of the jacket portion 38 are connected to the tank 50, and whole discharged gas and water from the pressure vessel 32 are collected in the tank 50. Since the water from the outside is supplied to the tank 50 from the branch pipe 61 of the water piping 42 as described above, the discharged gas and water at the high temperature from the pressure vessel 32 are cooled down to the predetermined temperature. Therefore, unlike the conventional devices, without providing the processing device of the discharged gas and water at the high temperature, the tank for supplying the water to the water ejector 48 can also perform a cooling process on the discharged gas and water at the high temperature.

The tank 50 is provided with the temperature sensor 67 for detecting a temperature of the water stored in the tank 50, and temperature data detected by the temperature sensor 67 is input to the control unit 68.

The control unit 68 includes memories such as a ROM and a RAM and a processor such as a CPU, and performs action control of the steam sterilizer 30 according to the present embodiment. A control program is previously recorded in the memory, and the processor executes the control action based on the control program.

Based on the temperature data input from the temperature sensor 67, the control unit 68 controls opening/closing of the valve 62 for opening/closing the branch pipe 61. When the water temperature in the tank detected by the temperature sensor 67 is lower than a previously-set predetermined temperature, the control unit 68 outputs a control signal to close the valve 62. When the water temperature in the tank detected by the temperature sensor 67 is the previously-set predetermined temperature or higher, the control unit 68 outputs the control signal to open the valve 62 and introduces the water from the outside into the tank 50.

As described above, based on the water temperature in the tank 50, an amount of water supply from the outside can be controlled to adjust the water temperature in the tank 50. If the water at a high temperature from the pressure vessel 32 can be cooled to 60° C. or less, the water can be normally discharged as it is.

The tank 50 is provided with a level sensor 69 for detecting a water level in the tank 50. The level sensor 69 is connected to the control unit 68 and communicates a detection signal to the control unit 68.

When it is detected by the level sensor 69 that the water level in the tank 50 is at a predetermined position or lower, the control unit 68 outputs the control signal to open the valve 62 and introduces the water from the outside into the tank 50.

As described above, the water in a previously-set amount or more can be always stored in the tank 50.

Figure 3:
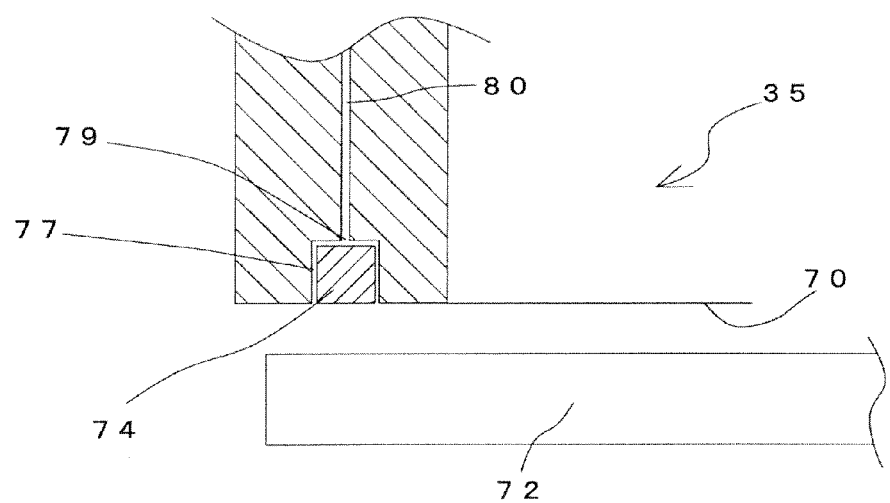
FIG. 3 is an explanation diagram illustrating a configuration of a vicinity of an opening portion of a pressure can body

FIG. 3 is a schematic diagram illustrating a vicinity of the opening portion of the pressure vessel 32.

As illustrated in FIG. 3, the pressure vessel 32 is formed with an opening portion 70 for opening the inner can 35 and provided with a door 72 for opening/closing the opening portion 70.

Since, when the door 72 is closed, the inside of the inner can 35 needs to be sealed, a packing 74 in contact with an inner face of the door 72 is provided at a periphery of the opening portion 70 of the pressure vessel 32. The packing 74 is made of silicone rubber or the like.

The packing 74 is movably stored in a packing-storing groove 77 formed at the periphery of the opening portion 70 of the pressure vessel 32.

At a rear edge portion (edge portion in an opposite direction of the side of the opening portion) of the packing-storing groove 77, a steam-supply hole 79 for supplying the saturated water vapor is formed. A branch pipe 80 branched from the steam piping 41 is connected to the steam-supply hole 79 to supply the saturated water vapor generated in the steam-generating device 40. In other words, the packing 74 is moved by the saturated water vapor supplied from the branch pipe 80.

The branch pipe 80 is provided with a valve 81 for opening/closing the branch pipe 80 to control movement of the packing 74 caused by the saturated water vapor according to an opening/closing control of the valve 81.

The opening/closing control of the valve 81 can be executed according to the control signal from the control unit 68. In other words, in the process in which the inner can 35 is required to be sealed with the packing 74, the control unit 68 outputs an opening signal to the valve 81 to discharge the saturated water vapor into the packing-storing groove 77, and the packing 74 is moved with the saturated water vapor to seal the door 72.

Further, when the process in which the inner can 35 is not required to be sealed is performed, the control unit 68 outputs a closing signal to the valve 81 to stop supplying the saturated water vapor to the packing-storing groove 77.

As described above, according to the present embodiment, since the saturated water vapor is used to drive the packing 74, even if a small amount of the saturated water vapor should leak via the packing 74 into the inner can 35, the sterilization cannot be failed, since the same saturated water vapor is used as that of the sterilization agent to be introduced into the inner can 35.

The saturated water vapor used to drive the packing 74 is discharged via either of a discharging pipe 92 connected to the tank 50 and a discharging pipe 93 connected to an absorbing portion of the water ejector 48. When the saturated water vapor is discharged via the discharging pipe 93 connected to the absorbing portion of the water ejector 48, the packing 74 is absorbed by the water ejector 48 and the protruded packing 74 is stored in the packing-storing groove 77.

Further, a discharging pipe 92 is provided with the valve 90 and a discharging pipe 93 is provided with the valve 91. Each of the valve 90 and the valve 91 is controlled to be opened/closed so that whether the discharged gas of the saturated water vapor after driving the packing 74 is directly discharged to the tank 50 or absorbed by the water ejector 48 can be selected.

The water ejector 48 may take longer to perform discharging compared with the vacuum pump used by the conventional steam sterilizer.

On the other hand, since the water ejector 48 according to the present embodiment discharges the saturated water vapor in the pressure vessel 32, the saturated water vapor becomes easily condensed by coming into contact with the pressurized water from the tank 50 in the water ejector 48. Therefore, when the saturated water vapor is discharged as described in the present embodiment rather than when normal gas is discharged, by the water ejector, a discharging speed can be improved.

Further, to improve the discharging speed by discharging the saturated water vapor as much as possible, when a sterilization process and so on in which the normal air is also included in the inner can 35 is started, it is preferable that the saturated water vapor be supplied in the inner can 35 for a certain time. With the process as described above, the air in the inner can 35 is replaced with the saturated water vapor and then a discharging time by the water ejector 48 can be shortened. Further, effects can be also acquired in which a replacement efficiency of the air in the inner can 35 with the saturated water vapor is increased to improve the sterilization effect in the sterilization process.

Figure 4:
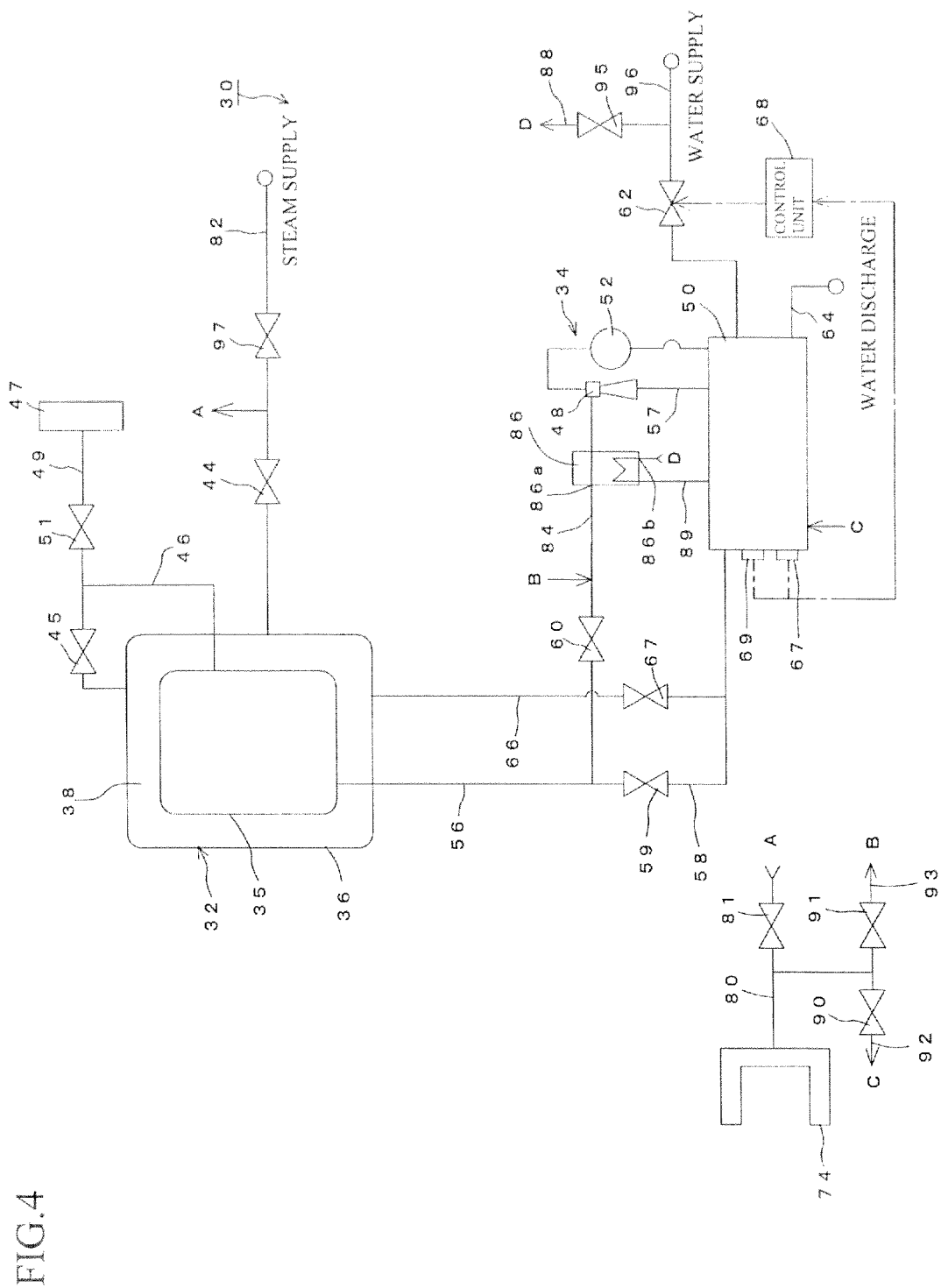
FIG. 4 is a schematic line diagram of a second embodiment of the steam sterilizer.

Next, a second embodiment of the present invention will be described. FIG. 4 is a schematic line diagram illustrating the second embodiment of the present invention. The same reference symbols are applied to the same components as those in the first embodiment described above, and the explanations may be omitted.

First, according to the present embodiment, the steam generator is not provided, and thus the saturated water vapor is supplied from the outside of the steam sterilizer 30 into the pressure vessel 32 via a steam piping 82. As an outer device connected with the steam piping 82, any device can be adopted as long as it can generate the saturated water vapor.

The steam piping 82 is provided with steam-supply valves 44, 97 for controlling introduction of the saturated water vapor into the jacket portion 38 by opening/closing the steam piping 82.

The vacuum-generating means 34 according to the present embodiment includes the water ejector 48, the tank 50 for storing the supply water supplied from the outside, and the pump 52 for supplying the supply water in the tank 50 to the water ejector 48. A gas and water discharging pipe 84 for making flow the discharged gas and water from the pressure vessel 32 introduced into the water ejector 48 is provided with condensing means 86 for condensing the water vapor in the discharged gas.

The condensing means 86 according to the present embodiment adopts a heat exchanger. Any heat exchanger may be adopted. A heat exchanger of a plate type is adopted herein that exchanges heat by alternately flowing fluid at a high temperature and fluid at a low temperature among plates including a plurality of layers.

The heat exchanger 86 includes a high-temperature fluid inlet 86a for introducing the discharged gas at a high-temperature from the pressure vessel 32 and a low-temperature fluid inlet 86b for introducing fluid at a lower temperature than the discharged gas at the high temperature to exchange the heat between the fluid at the high temperature and the fluid at the low temperature.

According to the present embodiment, as the fluid at the low temperature to be introduced into the heat exchanger 86, water introduced from the outside to the tank 50 is used. More specifically, at a middle portion of water piping 96 connected to the tank 50, a branch pipe 88 is provided. The branch pipe 88 is connected to the low-temperature fluid inlet 86b of the heat exchanger 86 and the water from the outside is used for exchanging the heat as the fluid at the low temperature. Further, to control the supply of the water to the heat exchanger 86, at a middle portion of the branch pipe 88, a valve 95 is provided.

Furthermore, the water raised in temperature due to the heat exchange by the heat exchanger 86 is introduced into the tank 50 via a piping 89.

The discharged gas from the pressure vessel 32 that has passed the heat exchanger 86 and has been cooled is in a state where the water vapor is condensed, and introduced into a middle portion of the nozzle 55 of the water ejector 48.

As described above, since the water vapor in the discharged gas from the pressure vessel 32 is condensed in a phase prior to being absorbed by the water ejector 48, it does not have to be considered that the water vapor is condensed by contacting the water by the water ejector 48. In other words, even if the water temperature of the water supplied from the tank 50 to the water ejector 48 is high (e.g., approximately 40° C. to 60° C.), it would not give adverse effects on the discharging speed and the vacuum-reaching level. With this arrangement, to decrease the water temperature in the tank 50, a great amount of water does not have to be introduced from the water piping 96, thereby saving the amount of water usage.

As the configuration in which, before being introduced into the water ejector 48, the water vapor in the discharged gas in the pressure vessel 32 is condensed, the configuration is not limited to the above-described heat-exchanger.

For example, a heat exchanger of a fin type may be adopted, and any configuration may be adopted as long as the configuration can condense the water vapor in the gas.

What is claimed is:

1. A steam sterilizer comprising:
    a pressure vessel which stores an object to be sterilized and in which sterilization is performed with water vapor supplied from a steam piping and which has a double-can structure constituted by an outer can and an inner can;
    vacuum-generating means which is connected to the pressure vessel and brings an inside of the inner can of the pressure vessel into a vacuum state;
    wherein the vacuum-generating means includes:
        a water ejector,
        a tank for storing supply water supplied from an outside,
        a pipe for introducing supply water from the outside to the tank,
        a control valve for controlling a flow of supply water toward the pipe,
        a pump for supplying supply water in the tank to the water ejector,
        a temperature sensor for detecting a temperature in the tank,
        a level sensor for detecting a water level in the tank,
        a gas and water discharging pipe for discharging a gas and water from the inner can of the pressure vessel, the gas and water discharging pipe being connected to the water ejector;
    condensing means for condensing water vapor in discharged gas from the pressure vessel, the condensing means being provided to the gas and water discharging pipe, which is connected to the water ejector, and located on an upstream side of the water ejector;
    a control unit operable to open the control valve to introduce supply water from the outside in a case where it is detected that the temperature detected by the temperature sensor due to the introduction of the discharged gas and water from the pressure vessel is higher than a predetermined threshold value and that a water level detected by the level sensor is at or lower than a predetermined level;
    a branch pipe branched from a part of the gas and water discharging pipe coupled to the water ejector and is coupled to the tank; and
    a drain-discharging pipe coupled to the tank and a jacket portion which is provided between the inner can and the outer can of the pressure vessel,
    wherein a whole of discharged gas and water from the pressure vessel is collected in the tank.

2. The steam sterilizer according to claim 1, wherein the pipe for introducing the supply water from the outside into the tank is connected to the water discharging pipe of the water ejector.

3. The steam sterilizer according to claim 1, wherein
    a door for opening/closing an opening portion is provided for the pressure vessel,
    a packing in contact with an inner face of the door when the door is closed is provided at a periphery of the opening portion of the pressure vessel, and
    a steam piping is branched and arranged inside the packing so that, when the door is closed, the packing is pressed and moved to the inner face of the door by the water vapor from the steam piping.

4. The steam sterilizer according to claim 2, wherein
    a door for opening/closing an opening portion is provided for the pressure vessel,
    a packing in contact with an inner face of the door when the door is closed is provided at a periphery of the opening portion of the pressure vessel, and
    a steam piping is branched and arranged inside the packing so that, when the door is closed, the packing is pressed and moved to the inner face of the door by the water vapor from the steam piping.

5. The steam sterilizer according to claim 1,
    wherein the condensing means is a heat exchanger capable of exchanging heat between the supply water from the outside and the discharged gas from the pressure vessel.

6. A steam sterilizer comprising:
    a pressure vessel which stores an object to be sterilized and in which sterilization is performed with water vapor supplied from a steam piping; and
    vacuum-generating means which is connected to the pressure vessel and brings an inside of the pressure vessel into a vacuum state,
    wherein the vacuum-generating means includes:
        a water ejector to which a gas and water discharging pipe from the pressure vessel is connected,
        a tank for storing supply water supplied from an outside,
        a pipe for introducing the supply water from the outside to the tank,
        a control valve for controlling a flow of the supply water toward the pipe,
        a pump for supplying supply water in the tank to the water ejector,
        a water-discharging pipe connecting an outlet of a nozzle of the water ejector to the tank,
        a temperature sensor for detecting a temperature in the tank,
        a level sensor for detecting a water level in the tank,
    condensing means for condensing water vapor in discharged gas from the pressure vessel, the condensing means being provided to the gas and water discharging pipe and located on an upstream side of the water ejector, and
    a control unit operable to open the control valve to introduce supply water from the outside in a first case where it is detected that a temperature detected by the temperature sensor due to the introduction of the discharged gas and water from the pressure vessel is higher than a threshold value and, in a second case where it is detected that a water level detected by the level sensor is at or lower than a predetermined level.

7. The steam sterilizer according to claim 6, wherein the pipe for introducing the supply water from the outside into the tank is connected to the water discharging pipe of the water ejector.

8. The steam sterilizer according to claim 6, wherein
    a door for opening/closing an opening portion is provided for the pressure vessel, a packing in contact with an inner face of the door when the door is closed is provided at a periphery of the opening portion of the pressure vessel, and a steam piping is branched and arranged inside the packing so that, when the door is closed, the packing is pressed and moved to the inner face of the door by the water vapor from the steam piping.

9. The steam sterilizer according to claim 7, wherein a door for opening/closing an opening portion is provided for the pressure vessel, a packing in contact with an inner face of the door when the door is closed is provided at a periphery of the opening portion of the pressure vessel, and a steam piping is branched and arranged inside the packing so that, when the door is closed, the packing is pressed and moved to the inner face of the door by the water vapor from the steam piping.

10. The steam sterilizer according to claim 6, wherein the condensing means is a heat exchanger capable of exchanging heat between the supply water from the outside and the discharged gas from the pressure vessel.

* * * * *